(12) United States Patent
Place

(10) Patent No.: US 6,284,262 B1
(45) Date of Patent: *Sep. 4, 2001

(54) COMPACT DOSAGE UNIT FOR BUCCAL ADMINISTRATION OF A PHARMACOLOGICALLY ACTIVE AGENT

(76) Inventor: Virgil A. Place, P.O. Box 44555 - 10 Ala Kahua, Kawaihae, HI (US) 96743

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/236,892

(22) Filed: Jan. 26, 1999

(51) Int. Cl.$^7$ .................................................. A61K 9/22
(52) U.S. Cl. ............................................ 424/435; 424/468
(58) Field of Search ...................................... 424/435, 468

(56) References Cited

U.S. PATENT DOCUMENTS

| | | |
|---|---|---|
| 4,704,285 | 11/1987 | Alderman . |
| 4,755,386 | 7/1988 | Hsiao et al. . |
| 4,764,378 | 8/1988 | Keith et al. . |
| 4,877,774 | 10/1989 | Pitha et al. . |
| 5,053,032 | 10/1991 | Barclay et al. . |
| 5,135,752 | 8/1992 | Snipes . |
| 5,242,391 | 9/1993 | Place et al. . |
| 5,346,701 | 9/1994 | Heiber et al. . |
| 5,516,523 | 5/1996 | Heiber et al. . |
| 5,543,154 | * 8/1996 | Rork et al. . |
| 5,639,743 | 6/1997 | Kaswan et al. . |

OTHER PUBLICATIONS

Bhasin et al. (1997), "Emerging Issues in Androgen Replacement Therapy," Journal of Clinical Endocrinology and Metabolism, 82(1):3–8.

* cited by examiner

Primary Examiner—Diana Dudash
Assistant Examiner—Alysia Berman
(74) Attorney, Agent, or Firm—Dianne E. Reed; Reed & Associates

(57) ABSTRACT

A simple and compact buccal dosage unit is provided for administering a pharmacologically active agent to a mammalian individual. The buccal dosage unit comprises the active agent to be administered, a polymeric carrier that bioerodes and provides for delivery of the androgenic agent over a predetermined time period, and, preferably, a lubricant such as magnesium stearate. The dosage units are ideal for administering drugs that have low oral bioavailability but are nevertheless potent and can thus be administered in small quantities, i.e., at low dosages, using the compact systems. Methods for administering active agents using the dosage units are provided as well.

38 Claims, 4 Drawing Sheets

COMPACT DOSAGE UNIT FOR BUCCAL ADMINISTRATION OF A PHARMACOLOGICALLY ACTIVE AGENT

TECHNICAL FIELD

This invention relates generally to the field of buccal drug delivery, i.e., to the transmucosal administration of pharmacologically active agents through the buccal mucosa. The invention provides a novel dosage unit for administering a drug through the buccal mucosa, and additionally provides therapeutic methods involving use of the buccal dosage units. The invention finds utility in a variety of contexts, including, but not limited to, delivery of steroid drugs in hormone replacement therapy, in the treatment of androgen-responsive disorders, in the treatment of male sexual dysfunction, and as contraceptive agents, and delivery of macromolecular drugs such as proteins, peptides, peptide fragments and polysaccharides.

BACKGROUND

There is an ongoing need in the pharmaceutical field to find effective ways of administering drugs that have low oral bioavailability. That is, a number of drugs are partially or completely metabolized in the liver and/or gastrointestinal tract, and cannot, therefore, be administered orally to achieve the desired therapeutic effect. Parenteral administration, i.e., injection, is one option, but not a route that many patients would find acceptable. Rectal and vaginal suppositories are also problematic from the standpoint of patient acceptance. Transdermal drug delivery has proved to be effective for a few drugs, but the vehicles and skin permeation enhancers typically required in transdermal systems can lead to skin irritation and/or sensitization, and the adhesive patches can be unpleasant to remove, leaving sensitive, discolored areas on the skin for some time after the patches are removed.

Buccal drug delivery, i.e., administration of a drug through the buccal mucosa, has also been described. Prior to the present invention, however, buccal drug delivery systems have proved to be problematic. A non-erodible backing layer is typically present that can lodge in the pharynx if a buccal tablet or patch is inadvertently swallowed. Prior buccal tablets or patches have also been relatively large and have tended to move about within a patient's mouth, both factors resulting in patient discomfort. More recently described buccal dosage forms are somewhat complicated to manufacture, insofar as distinct layers with different chemical and physical properties need to be made and incorporated into a single dosage form. See, for example, U.S. Pat. No. 5,346,701 to Heiber et al., which describes a bilayer tablet comprising a first, adhesive layer containing an adhesive polymer, a filler, an excipient, a lubricant, flavor, dye, etc., and an adjacent second layer containing drug, permeation enhancer, taste-masking agents, stabilizers, enzyme inhibitors, and possibly other components.

The present invention overcomes the disadvantages associated with prior buccal drug delivery systems, as will be discussed in detail herein. The buccal dosage unit of the invention is a highly effective, highly efficient, compact tablet that in its simplest form contains only drug and excipient. The dosage unit adheres well to the buccal mucosa, is small enough so as not to cause patient discomfort, and completely hydrolyzes within the mouth, i.e., gradually and completely bioerodes throughout the drug delivery period. The dosage unit may be used to administer any one of a number of pharmacologically active agents.

One use of the buccal dosage units in the administration of steroidal agents, particularly androgenic agents, such as in male hormone replacement therapy, in male contraceptive compositions, in the treatment of androgen-responsive disorders, and in the treatment of male sexual dysfunction.

Androgens are the hormones that cause most of the masculinizing changes that occur in males during puberty. *Harrison's Principles of Internal Medicine*, $12^{th}$ Edition (New York, N.Y.: McGraw Hill, Inc., 1991). Testosterone is secreted by the testis and adrenal gland and is the main androgen present in the plasma of men. See, e.g., Goodman & Gilman's *The Pharmacological Basis of Therapeutics*, $9^{th}$ Edition (New York, N.Y.: McGraw Hill, Inc., 1996). As explained in the aforementioned text, the concentration of testosterone in the plasma of human males is relatively high throughout several periods of life, including the period of embryonic development in which the male phenotypic differentiation takes place, the neonatal period, and during adult sexual life. Prior to puberty, concentrations of testosterone are in the plasma are low, on the order of 20 nanograms/deciliter (ng/dl) or less. In adults, plasma testosterone concentrations range from about 300 to 1000 ng/dl, and the rate of production is 2.5 to 11 mg per day. Approximately 40% of the testosterone is bound to sex hormone-binding protein and about 2% is free, or unbound; the remainder is bound to albumin and other proteins. Testosterone is secreted in a pulsatile manner, so that normal testosterone levels fluctuate within a circadian pattern during the course of a day. See, e.g., Goodman & Gilman's, supra.

At puberty, testosterone levels begin to rise in boys, reaching adult levels by the age of about seventeen. See, e.g., *Harrison's Principles of Internal Medicine*, supra. The rise in testosterone levels during puberty catalyzes a variety of anatomical and developmental changes, including maturation of the accessory organs of male reproduction, development of facial hair, regression of the scalp line, appearance of pubic hair, and increased growth of muscle and connective tissue. Altered testicular steroid levels can result from hypothalamic-pituitary disorders or testicular defects. For example, failure of the testis to develop or function, resulting in hypogonadism, may result from a deficiency of gonadotropin or from primary testicular failure. If hypogonadism occurs prior to puberty, development of secondary sexual characteristics will be impaired or absent. In the adult, hypogonadism results in osteopenia, regression of the prostate and seminal vesicles, reduction in the volume of semen, and loss of muscle mass, strength and vigor. Loss of steroid production also results in psychological depression and reduction or absence of the libido, both of which are associated with sexual dysfunction. See, e.g., *Harrison's Principles of Internal Medicine*, supra.

Testosterone is well absorbed after its oral administration but is quickly degraded during its passage through the liver and intestine. Therefore, it is not possible to achieve therapeutic blood levels of testosterone via oral administration. $17\alpha$-alkylated derivatives of testosterone can be administered orally and are resistant to hepatic degradation, but are not recommended for clinical use due to their high potential for hepatoxicity. Bhasin et al. (1997) *J. of Clin. Endoc. and Met.* 82(1):3. Transdermal delivery of testosterone has been described, but requires flux enhancement with skin permeation enhancers. As noted above, skin permeation enhancers frequently result in irritation and sensitization of the skin, and, with some enhancers, e.g., dimethyl formamide and dimethyl sulfoxide, the potential for toxicity is not insignificant. Accordingly, there remains a need in the art to provide a more effective method for administering androgenic agents such as testosterone.

Drug therapy involving buccal administration of steroid hormones has been described. For example, U.S. Pat. No. 4,755,386 to Hsiao et al. generally describes the buccal administration of various medicaments, including estrogens, progestins and androgens. The buccal tablets, weighing on the order of 50 mg, contain adhesive, disintegrant and excipient in addition to the active agent. Additionally, U.S. Pat. No. 4,764,378 to Keith et al. describes rapidly disintegrating dosage forms utilizing a combination of high and low molecular weight polyethylene glycols; the dosage forms, which are preferably 50 mg to 100 mg tablets, may be administered orally or through the buccal mucosa. Similarly, U.S. Pat. No. 5,135,752 to Snipes et al. describes buccal delivery systems containing polyethylene glycols of varying molecular weights for the delivery of methyl testosterone or estradiol ($E_2$). In U.S. Pat. No. 4,877,774 to Pitha et al., crystalline complexes of steroid hormones and gamma-cyclodextrin are described for administration of steroids through mucosal tissue.

The buccal drug delivery systems of the present invention are, however, new and completely unsuggested by the art. Applicant's invention is premised on the discovery that a simple, compact, completely hydrolyzable buccal dosage unit, containing, in a preferred embodiment, only the pharmacologically active agent to be administered and an excipient, provides for highly efficient, highly effective drug delivery.

SUMMARY OF THE INVENTION

Accordingly, it is a primary object of the invention to address the aforementioned need in the art by providing a novel dosage unit for administering a pharmacologically active agent transmucosally, through the buccal mucosa.

It is another object of the invention to provide a simple, compact buccal dosage unit that gradually and completely bioerodes over a predetermined time period, typically in the range of 4 to 24 hours.

It is still another object of the invention to provide such a buccal dosage unit that is compositionally substantially uniform in nature.

It is yet another object of the invention to provide such a buccal dosage unit containing only a pharmacologically active agent to be administered, a polymeric carrier, and, optionally, a lubricant to facilitate manufacture of the unit.

It is a further object of the invention to provide such a buccal dosage unit wherein the active agent is a potent drug that has relatively low bioavailability when administered orally.

It is an additional object of the invention to provide such a buccal dosage unit wherein the active agent is a steroid, a macromolecular drug such as a protein, peptide, peptide fragment or polysaccharide, nicotine or fentanyl.

It is still an additional object of the invention to provide a method for administering a pharmacologically active agent to a mammalian individual using a buccal dosage unit as described herein.

Still additional objects of the invention include methods for effecting male contraception, providing male hormone replacement therapy, treating male sexual dysfunction, and treating androgen-responsive disorders, by using the dosage units of the invention to administer an androgenic agent such as testosterone through Additional objects, advantages and novel features of the invention will be set forth in part in the description which follows, and in part will become apparent to those skilled in the art upon examination of the following, or may be learned by practice of the invention.

Accordingly, in a first embodiment, a pharmaceutical composition is provided in the form of a simple, compact buccal dosage unit comprising a therapeutically effective amount of a pharmacologically active agent in a bioerodible polymeric carrier, wherein the carrier is such that it enables the dosage unit to adhere to the buccal mucosa. Following application to the buccal mucosa, gradual and complete erosion of the unit occurs over a predetermined time period, thus providing drug delivery throughout that time period. In a preferred embodiment, the dosage unit contains only the active agent to be administered and the polymeric carrier. However, other components, particularly a lubricant, may be incorporated to facilitate manufacture of the unit or if otherwise found to be necessary or desirable. The buccal dosage units are typically far smaller than conventional buccal delivery systems—the present tablets are on the order of 5–20 mg, typically 10–15 mg—and do not require a plurality of excipients, disintegrants, adhesives, or the like, nor are fragrances or permeation enhancers necessary. Accordingly, the novel dosage units are more comfortable than conventional systems because of their compact size. The units also tend to stay in place after being affixed to the buccal mucosa. While the dosage units are designed to erode and thus deliver the active agent over a time period in the range of about 4 hours to 24 hours, 20- to 24-hour dosage units are preferred for administration of an androgenic agent. The preferred androgenic agent is testosterone, or a pharmacologically acceptable derivative, analog, ester or salt thereof.

In another embodiment of the invention, a method is provided for administering a pharmacologically active agent to a mammalian individual using the aforementioned buccal dosage units, to treat any disorder, condition, disease or dysfunction for which the active agent is indicated. An androgenic agent may be administered, for example, to treat sexual dysfunctional in a mammalian male, to provide male hormone replacement therapy, to treat androgen-responsive disorders (e.g., primary or secondary hypogonadism), or the like. The active agent is administered by affixing a dosage unit as provided herein to the buccal mucosa of the individual undergoing treatment, and allowing the dosage unit to remain in place until erosion thereof and thus drug delivery is complete. Preferably, the dosage unit is affixed to the upper gum area in a region defined as extending from the first bicuspid on the left to the first bicuspid on the right; an alternative preferred location for the dosage unit is the inner lip area opposing the aforementioned upper gum area.

A further embodiment of the invention relates to a kit to assist an individual in buccal drug administration. Generally, the kit includes the following components: a buccal dosage unit comprising a pharmacologically active agent and a bioerodible polymeric carrier; a container housing the dosage unit prior to use; and written instructions for carrying out administration of the active agent for the intended therapeutic purpose.

DETAILED DESCRIPTION OF THE INVENTION

Figure 1:
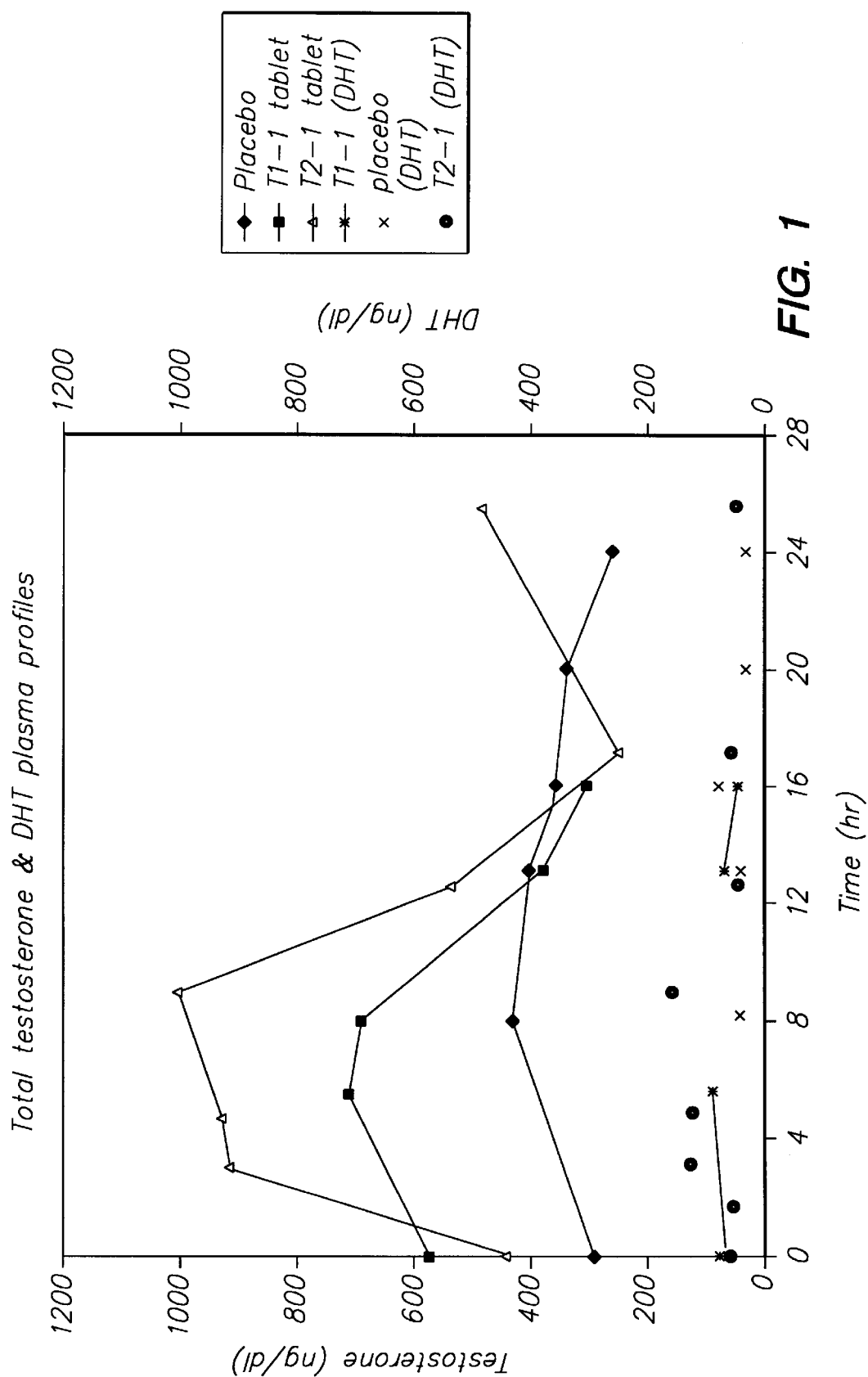
FIG. 1 is a graph illustrating testosterone and dihydrotestosterone plasma levels as a function of time, following administration of either a placebo or a T1-1 or T2-1 buccal testosterone tablet, as described in Example 3.

Before describing the present invention in detail, it is to be understood that this invention is not limited to particular drugs, vehicles or indications, as such may vary. It is also to be understood that the terminology used herein is for the purpose of describing particular embodiments only, and is not intended to be limiting.

It must be noted that, as used in this specification and the appended claims, the singular forms "a", "an" and "the" include plural referents unless the context clearly dictates otherwise. Thus, for example, reference to "an active agent" includes a mixture of two or more active agents, reference to "a polymeric carrier" includes mixtures of two or more suitable polymeric carriers, and the like.

In describing and claiming the present invention, the following terminology will be used in accordance with the definitions set out below.

The terms "drug" or "pharmacologically active agent" or "active agent" as used herein refer to a compound or composition of matter which, when administered to an organism (human or animal) induces a desired pharmacologic and/or physiologic effect by local and/or systemic action. A "macromolecular" drug as used herein generally refers to a drug having a molecular weight greater than about 250 Daltons, typically greater than about 500 Daltons, and is normally a peptide, peptide fragment, protein or polysaccharide.

By "buccal" drug delivery is meant delivery of a drug by passage of a drug through the buccal mucosa into the bloodstream. Preferably, buccal drug delivery is effected herein by placing the buccal dosage unit on the upper gum or opposing inner lip area of the individual undergoing drug therapy.

"Penetration enhancement" or "permeation enhancement" as used herein relates to an increase in the permeability of the buccal mucosal tissue to a pharmacologically active agent, i.e., so that the rate at which the drug permeates through the mucosal tissue is increased.

"Excipients" or "vehicles" as used herein refer to any excipients or vehicles suitable for buccal drug administration, and include any such materials known in the art, e.g., any liquid, gel, solvent, liquid diluent, solubilizer, or the like, which is nontoxic and which does not interact with other components of the composition in a deleterious manner.

By an "effective" or "therapeutically effective" amount of a drug or pharmacologically active agent is meant a nontoxic but sufficient amount of the drug or agent to provide the desired effect. An "effective" amount of a permeation enhancer as used herein means an amount that will provide the desired increase in the rate at which an active agent passes through the tissue of the buccal mucosa.

"Compact" as used herein refers to a buccal dosage unit that is preferably no larger than about 5 mm in diameter and 2 mm in height, so that the unit occupies at most about 40 mm$^3$, typically weighs less than about 40 mg (preferably 5 to 20 mg, more preferably 10 to 15 mg), and has a contact surface area of no more than 20 mm$^2$.

The terms "erodible" and "bioerodible" as used herein refer to a compound or composition that hydrolyzes upon contact with the buccal mucosa.

The term "androgen-responsive disorder" includes any disease or condition that may be treated by administration of androgens as provided herein. A particular example of an androgen-responsive disorder is hypogonadism.

The term "sexual dysfunction" is generally used to mean erectile dysfunction in mammalian males, and is intended to include any and all types of erectile dysfunction, including: vasculogenic, neurogenic, endocrinologic and psychogenic impotence ("impotence" is used here in its broadest sense to indicate an inability a periodic or consistent inability to achieve or sustain an erection of sufficient rigidity for sexual intercourse; see U.S. Pat. No. 5,242,391 to Place et al., cited supra); Peyronie's syndrome; priapism; premature ejaculation; and any other condition, disease or disorder, regardless of cause or origin, which interferes with at least one of the three phases of human sexual response, i.e., desire, excitement and orgasm (see Kaplan, *Disorders of Sexual Desire* (New York, N.Y.: Brunner Mazel Book Inc., 1979)).

The terms "treating" and "treatment" as used herein refer to reduction in severity and/or frequency of symptoms, elimination of symptoms and/or underlying cause, prevention of the occurrence of symptoms and/or their underlying cause, and improvement or remediaton of damage. Thus, for example, the present method of "treating" an androgen-responsive disorder, as the term is used herein, encompasses both prevention of the disorder in a predisposed individual and treatment of the disorder in a clinically symptomatic individual. Similarly, "treatment" of sexual dysfunction encompasses both prevention and treatment of sexual dysfunction.

In one embodiment, then, a pharmaceutical composition is provided in the form of a buccal dosage unit for the administration of a pharmacologically active agent. The dosage unit comprises (a) a therapeutically effective amount of the active agent and (b) a bioerodible polymeric carrier as will be described in detail below. The dosage unit is fabricated so as to erode gradually over a predetermined time period, wherein drug delivery is provided essentially throughout. The time period is typically in the range of 4 hours to 24 hours; that is, for a 4-hour unit, erosion will occur throughout a 4-hour period and be complete at the 4-hour point, while for a 24-hour unit, erosion will occur throughout a 24-hour period and be complete at the 24-hour point. The buccal dosage unit may further comprise a lubricant to facilitate manufacture, e.g., magnesium stearate or the like. Additional components that may be included in the buccal dosage unit, but are neither required nor preferred, are flavorings, permeation enhancers, diluents, binders, and the like. As a buccal drug delivery system, the novel dosage unit avoids the disadvantages encountered with oral drug administration, e.g., degradation of the agent by fluids present in the gastrointestinal tract and/or first-pass inactivation in the liver. In addition, because of its compact size, the unit is not associated with the discomfort encountered with larger, conventional buccal drug delivery systems. Also, the units are convenient in that the wearer need replace a spent unit only once or twice daily, i.e., with 24-hour or 12-hour systems, respectively; a 12-hour unit to be applied once in the morning and once in the evening is optimal. Finally, because of the compositional simplicity of the unit—in a preferred embodiment, the unit contains only the active agent and the polymeric carrier—manufacture of the dosage form is straightforward and economical.

The pharmacologically active agents that may be used in conjunction with the invention are typically drugs that have low oral bioavailability and cannot, therefore, be administered orally. Potent drugs, i.e., drugs that are effective at low dosages are preferred, so that a smaller quantity of active agent can be used; drugs that require higher dosages, necessitating a larger dosage unit, should be avoided. "Potent" drugs in the present context are drugs that are effective at a dosage of less than 15 mg in a 24-hour period.

In general, suitable pharmacologically active agents for use herein include, but are not limited to: anti-infectives such as antibiotics and antiviral agents; analgesics and analgesic combinations; anesthetics; anorexics; antiarthritics; antiasthmatic agents; anticonvulsants; antidepressants; antidiabetic agents; antidiarrheals; antihistamines; antihypertensives; antiinflammatory agents; antimigraine preparations; antinauseants; antineoplastics; antiparkinsonism drugs; antipruritics; antipsychotics; antipyretics; antispasmodics; anticholinergics; calcium channel blockers; cardiovascular preparations; central nervous system stimulants; cough and cold preparations, including decongestants; diuretics; growth factors; growth hormones; hypnotics; immunosuppressives; muscle relaxants; parasympatholytics; psychostimulants; sedatives; sympathomimetics; vasodilating agents including general coronary, peripheral and cerebral vasodilators; steroid hormones; and tranquilizers.

Specific drugs and drug types that can be effectively delivered using the buccal dosage units of the invention include, but are not limited to, steroids such as androgens, estrogens, progestins and corticosteroids; macromolecular drugs such as proteins, peptides, peptide fragments, and polysaccharides; nicotine; and fentanyl.

Suitable androgens that may be used in the formulations of the present invention include, but are not limited to: the naturally occurring androgens and derivatives thereof, including androsterone, androsterone acetate, androsterone propionate, androsterone benzoate, androstenediol, androstenediol-3-acetate, androstenediol-17-acetate, androstenediol-3,17-diacetate, androstenediol-17-benzoate, androstenediol-3-acetate-17-benzoate, androstenedione, ethylestrenol, oxandrolone, nandrolone phenpropionate, nandrolone decanoate, nandrolone furylpropionate, nandrolone cyclohexanepropionate, nandrolone benzoate, nandrolone cyclohexanecarboxylate, stanozolol, dromostanolone, dromostanolone propionate, testosterone, dehydroepiandrosterone (DHEA; also termed "prasterone"), sodium dehydroepiandrosterone sulfate, 4-dihydrotestosterone (DHT; also termed "stanolone"), and 5α-dihydrotestosterone; pharmaceutically acceptable esters of testosterone and 4-dihydrotestosterone, typically esters formed from the hydroxyl group present at the C-17 position, including, but not limited to, the enanthate, propionate, cypionate, phenylacetate, acetate, isobutyrate, buciclate, heptanoate, decanoate, undecanoate, caprate and isocaprate esters; and pharmaceutically acceptable derivatives of testosterone such as methyl testosterone, testolactone, oxymetholone and fluoxymesterone. Testosterone per se is a particularly preferred androgenic agent for use in conjunction with the present invention. The aforementioned testosterone esters are commercially available or may be readily prepared using techniques known to those skilled in the art or described in the pertinent literature. (Generally, the 17-hydroxyl group of the testosterone molecule is caused to react with a suitable organic acid under esterifying conditions, such conditions typically involving the use of a strong acid such as sulfuric acid, hydrochloric acid, or the like, and a temperature sufficient to allow the reaction to proceed at reflux.)

Suitable estrogens that may be administered using the dosage units of the invention include synthetic and natural estrogens such as: estradiol (i.e., 1,3,5-estratriene-3,17β-diol, or "β-estradiol") and its esters, including estradiol benzoate, valerate, cypionate, heptanoate, decanoate, acetate and diacetate; 17α-estradiol; ethynylestradiol (i.e., 17α-ethynylestradiol) and esters and ethers thereof, including ethynylestradiol 3-acetate and ethynylestradiol 3-benzoate; estriol and estriol succinate; polyestrol phosphate; estrone and its esters and derivatives, including estrone acetate, estrone sulfate, and piperazine estrone sulfate; quinestrol; mestranol; and conjugated equine estrogens. Estradiol and ethynylestradiol are particularly preferred synthetic estrogenic agents for use in conjunction with the present invention.

Suitable progestins for use in the buccal drug delivery units of the invention include, but are not limited to, acetoxypregnenolone, allylestrenol, anagestone acetate, chlormadinone acetate, cyproterone, cyproterone acetate, desogestrel, dihydrogesterone, dimethisterone, ethisterone (17α-ethynyltestosterone), ethynodiol diacetate, flurogestone acetate, gestadene, hydroxyprogesterone, hydroxyprogesterone acetate, hydroxyprogesterone caproate, hydroxymethylprogesterone, hydroxymethylprogesterone acetate, 3-ketodesogestrel, levonorgestrel, lynestrenol, medrogestone, medroxyprogesterone acetate, megestrol, megestrol acetate, melengestrol acetate, norethindrone, norethindrone acetate, norethisterone, norethisterone acetate, norethynodrel, norgestimate, norgestrel, norgestrienone, normethisterone, and progesterone. Progesterone, cyproterone acetate, norethindrone, norethindrone acetate and levonorgestrel are preferred progestins.

Macromolecular drugs, as the term is used herein, are active agents having a molecular weight of at least about 250 Daltons, normally at least about 500 Daltons, and are typically proteins, peptides, peptide fragments, or polysaccharides. A preferred polysaccharide to be delivered buccally using the present dosage units is heparin.

With respect to proteins, peptides and peptide fragments, such macromolecular drugs may be delivered using the dosage units of the invention without regard to how the drugs are prepared, i.e., they may be naturally occurring, chemically synthesized or recombinantly produced. Specific examples of peptides and proteins that may be administered using the buccal dosage units of the invention include: calcitonin; clotting factors; CD4; colony stimulating factors, including granulocyte colony stimulating factor (G-CSF), macrophage colony stimulating factor (M-CSF), and granulocyte/macrophage colony stimulating factor (GM-CSF); erythropoietin; fibronectin; growth factors such as human growth factor (hGF), epidermal growth factor (EGF), insulin-like growth factor (IGF), nerve growth factor (NGF), fibroblast growth factor (FGF), and platelet-derived growth factor (PDGF); growth hormones, particularly human growth hormone (hGH) and somatropin; human chorionic gonadotropin (hCG); insulin; interferons, including interferon alpha-n3, beta-interferon and interferon gamma-1b; interleukins, particularly IL-1, IL-2, IL-3, IL-4 and IL-6; lymphokines; menotropins, i.e., follicle stimulating hormone (FSH) and luteinizing hormone (LH); monoclonal antibodies; neurotrophic factors; parathyroid hormone; somatostatin; thymosin alpha-1; thrombolytic agents and anticoagulants, such as antihemophiliac factor and Factor VIIa; tissue plasminogen activator (tPA); tumor necrosis factor (TNF); and vaccines, including gp 120, hepatitis vaccines, HIV immunotherapeutic vaccines, and malaria vaccines.

Still other active agents that can be administered using the buccal dosage units of the invention include nicotine and fentanyl.

The active agent may be incorporated into the present dosage units and thus administered in the form of a pharmaceutically acceptable derivative, analog, ester or salt, or the agent may be modified by appending one or more appropriate functionalities to enhance selected biological properties such as penetration through the mucosal tissue. In general, when the buccal dosage units are used to administer steroid drugs, particularly androgenic agents, esters are preferred relative to salts or other derivatives. Preparation of esters involves functionalization of hydroxyl and/or carboxyl groups which may be present, as will be appreciated by those skilled in the art of pharmaceutical chemistry and drug delivery. Esters can be reconverted to the free acids, if desired, by using conventional hydrogenolysis or hydrolysis procedures.

To administer the active agent in salt form, suitable pharmaceutically acceptable salts can be prepared using standard procedures known to those skilled in the art of synthetic organic chemistry and described, for example, by J. March, *Advanced Organic Chemistry: Reactions, Mechanisms and Structure*, 4th Ed. (New York: Wiley-Interscience, 1992). Acid addition salts are prepared from an active agent in the free base form (e.g., compounds having a neutral —$NH_2$ group) using conventional means, involving reaction with a suitable acid. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Preparation of basic salts of acid moieties which may be present (e.g., carboxylic acid groups) are prepared in a similar manner using a pharmaceutically acceptable base such as sodium hydroxide, potassium hydroxide, ammonium hydroxide, calcium hydroxide, magnesium hydroxide, trimethylamine, or the like.

For those active agents that are chiral in nature and can thus be in enantiomerically pure form or in a racemic mixture, the drug may be incorporated into the present dosage units either as the racemate or in enantiomerically pure form.

The quantity of active agent in the buccal dosage unit will depend on the potency of the agent and the intended dosage, which, in turn, is dependent on the particular individual undergoing treatment, the specific indication, and the like. Suitable doses of specific active agents will be known to those skilled in the art, or may be deduced from the literature in combination with the teaching of the present disclosure. By way of example, a typical daily dosage of testosterone for treatment of sexual dysfunction or other indications as discussed herein is in the range of about 4 to about 10 mg. The dosage unit will generally contain from approximately 40 wt. % to about 80 wt. % active agent, preferably on the order of 50 wt. % to about 75 wt. % active agent. The remainder of the composition is comprised of a carrier as will be described in detail below.

Ideally, the carrier comprises a polymer having sufficient tack to ensure that the dosage unit adheres to the buccal mucosa for the necessary time period, i.e., the time period during which drug is to be delivered to the buccal mucosa. Additionally, the polymeric carrier is gradually "bioerodible," i.e., the polymer hydrolyzes at a predetermined rate upon contact with moisture. The polymeric carrier is preferably sticky when moist, but not when dry, for convenience in handling. Generally, it is preferred that the weight average molecular weight ($M_w$) of the polymer be in the range of approximately 4,000 to 1,000,000, more preferably in the range of approximately 100,000 to 1,000,000. One of skill in the art will appreciate that the higher the molecular weight of the polymer, the slower the erosion time.

Any polymeric carriers can be used that are pharmaceutically acceptable, provide both a suitable degree of adhesion and the desired drug release profile, and are compatible with the drug to be administered and any other components that may be present in the buccal dosage unit. Generally, the polymeric carriers comprise hydrophilic (water-soluble and water-swellable) polymers that adhere to the wet surface of the buccal mucosa. Examples of polymeric carriers useful herein include acrylic acid polymers and co, e.g., those known as "carbomers" (Carbopol®, which may be obtained from B.F. Goodrich, is one such polymer). Other suitable polymers include, but are not limited to: hydrolyzed polyvinylalcohol; polyethylene oxides (e.g., Sentry Polyox® water soluble resins, available from Union Carbide); polyacrylates (e.g., Gantrez®, which may be obtained from GAF); vinyl polymers and copolymers; polyvinylpyrrolidone; dextran; guar gum; pectins; starches; and cellulosic polymers such as hydroxypropyl methylcellulose, (e.g., Methocel®, which may be obtained from the Dow Chemical Company), hydroxypropyl cellulose (e.g., Klucel®, which may also be obtained from Dow), hydroxypropyl cellulose ethers (see, e.g., U.S. Pat. No. 4,704,285 to Alderman), hydroxyethyl cellulose, carboxymethyl cellulose, sodium carboxymethyl cellulose, methyl cellulose, ethyl cellulose, cellulose acetate phthalate, cellulose acetate butyrate, and the like. The carrier may also comprise two or more suitable polymers in combination, for example, a carbomer combined in an approximately 1:5 to 5:1 ratio, by weight, with a polyethylene oxide.

It is preferred that the present dosage unit contain only active agent and polymeric carrier. However, it may be desirable in some cases to include one or more additional components. For example, a lubricant may be included to facilitate the process of manufacturing the dosage units; lubricants may also optimize erosion rate and drug flux. If a lubricant is present, it will represent on the order of 0.01 wt. % to about 2 wt. %, preferably about 0.01 wt. % to 0.5 wt. %, of the dosage unit. Suitable lubricants include, but are not limited to, magnesium stearate, calcium stearate, stearic acid, sodium stearylfumarate, talc, hydrogenated vegetable oils and polyethylene glycol. As will be appreciated by those skilled in the art, however, modulating the particle size of the components in the dosage unit and/or the density of the unit can provide a similar effect—i.e., improved manufacturability, and optimization of erosion rate and drug flux—without addition of a lubricant.

Other components may also be incorporated into the buccal dosage unit; however, it must be emphasized that such components are neither required nor preferred. Such additional optional components include, for example, one or more disintegrants, diluents, binders, enhancers, or the like. Examples of disintegrants that may be used include, but are not limited to, cross-linked polyvinylpyrrolidones, such as crospovidone (e.g., Polyplasdone® XL, which may be obtained from GAF), cross-linked carboxylic methylcelluloses, such as croscarmelose (e.g., Ac-di-sol®, which may be obtained from FMC), alginic acid, and sodium carboxymethyl starches (e.g., Explotab®, which may be obtained from Edward Medell Co., Inc.), methylcellulose, agar bentonite and alginic acid. Suitable diluents are those which are generally useful in pharmaceutical formulations prepared using compression techniques, e.g., dicalcium phosphate dihydrate (e.g., Di-Tab®, which may be obtained from Stauffer), sugars that have been processed by cocrystallization with dextrin (e.g., co-crystallized sucrose and dextrin such as Di-Pak®, which may be obtained from Amstar), lactone, calcium phosphate, cellulose, kaolin, mannitol, sodium chloride, dry starch, powdered sugar and the like. Binders, if used, are those that enhance adhesion. Examples of such binders include, but are not limited to, starch, gelatin and sugars such as sucrose, dextrose, molasses, and lactose. Permeation enhancers may also be present in the novel dosage units in order to increase the rate at which the active agent passes through the buccal mucosa. Examples of permeation enhancers include, but are not limited to, polyethylene glycol monolaurate ("PEGML"), glycerol monolaurate, lecithin, the 1-substituted azacycloheptan-2-ones, particularly 1-n-dodecylcyclaza-cycloheptan-2-one (available under the trademark Azone® from Nelson Research & Development Co., Irvine, Calif.), lower alkanols (e.g., ethanol), SEPA® (available from Macrochem Co., Lexington, Mass.), cholic acid, taurocholic acid, bile salt type enhancers, and surfactants such as Tergitol®, Nonoxynol-9® and TWEEN-80®. Preferred compositions of the invention, however, do not contain permeation enhancers.

Flavorings are not typically needed in the present drug dosage units, as the active agents do not, in general, have any taste. If for some reason a flavoring is desired, any suitable flavoring may be used, e.g., mannitol, lactose or artificial sweeteners such as aspartame. Coloring agents may be added, although again, such agents are not required. Examples of coloring agents include any of the water soluble FD&C dyes, mixtures of the same, or their corresponding lakes.

In addition, if desired, the present dosage units may be formulated with one or more preservatives or bacteriostatic agents, e.g., methyl hydroxybenzoate, propyl hydroxybenzoate, chlorocresol, benzalkonium chloride, or the like.

The present dosage units may be used to deliver a single active agent or two or more active agents in combination. In the latter case, each active agent may be delivered using an individual buccal dosage unit, with the buccal dosage units then used in combination. Preferably, the active agents are combined in a single buccal dosage unit.

In general, the dosage unit of the invention is compositionally a substantially homogeneous, substantially uniform formulation. By "substantially uniform" is meant that the dosage unit is not coated, does not have a backing, and does not contain a plurality of layers or other types of discrete segments. Rather, the substance of the dosage unit is similar throughout, so that the unit is essentially "monolithic" in nature.

In another embodiment of the invention, a method is provided for administering a pharmacologically active agent to a mammalian individual. The method generally comprises buccally administering the agent by affixing a dosage unit as described herein to the buccal mucosa of the individual and allowing the dosage unit to remain in place until erosion thereof—and thus drug delivery—is complete. Administration of an active agent in this way is useful in a variety of contexts, as will be readily appreciated by those skilled in the art. For example, the buccal administration of an androgenic agent using the dosage units of the invention may be used in hormone replacement therapy, particularly male hormone replacement therapy, in male contraception, in the treatment of androgen-responsive disorders such as hypogonadism, and in the treatment of male sexual dysfunction.

Hormone replacement therapy is generally called for in male individuals for whom testicular steroid production (e.g., testosterone) has been altered. By way of example, conditions associated with decreased or absent endogenous testosterone, such as primary hypogonadism (congenital or acquired) or secondary hypogonadism (again, congenital or acquired) may be treated by the methods and compositions defined herein. Alteration in testicular steroid production can be caused by, for example, hypothalamic-pituitary defects or testicular defects. Examples of hypothalamic-pituitary defects causing altered steroid production include, but are not limited to, panhypopituitarism, hypogonadotropic hypogonadism, Cushing's syndrome, Kolman's syndrome hyperprolactinemia, and hemochromatosis. Examples of testicular defects causing altered steroid production include, but are not limited to, developmental and structural defects, such as Klinefelter's syndrome and XX male syndrome. Examples of acquired testicular defects resulting in altered steroid production include, but are not limited to, viral orchitis, testicular failure, ablation or atrophy due to surgery, radiation, or thermal or physical testicular trauma, drugs (e.g., spironolactone, alcohol, ketoconazole, cyclophosphamide), autoimmunity, granulomatous disease, androgen resistance, and systemic disease (e.g., liver disease, renal failure, Sickle cell disease, neurological disease). Alternatively, the method and drug dosage units of the invention can be used to treat or inhibit the symptoms of osteoporosis, dry eye, or the wasting syndrome accompanying AIDS (e.g., unintentional weight loss, decrease in lean body mass).

In this latter embodiment, the buccal dosage unit will contain an androgenic agent in an amount suitable for providing hormone replacement therapy to a male in need of such treatment. Preferably, as described hereinabove, the dosage unit is capable of delivering about 4 to about 10 mg of the selected androgen, preferably testosterone, over a predetermined time period, typically in the range of about 4 hours to about 24 hours. Also as described earlier herein, the buccal dosage unit will contain approximately 40 wt. % to 80 wt. % active agent, preferably on the order of 50 wt. % to 75 wt. % active agent. A preferred buccal dosage unit of the invention incorporates testosterone, or a testosterone ester such as testosterone enanthate, testosterone propionate or testosterone cypionate, while in a particularly preferred embodiment the buccal dosage unit contains testosterone per se.

A method is also provided for treating androgen-responsive disorders (such as hypogonadism). Administration of the buccal dosage unit is carried out within the context of a dosing regimen so that a therapeutically effective amount of the active agent is delivered to mitigate or substantially prevent the symptoms associated with the androgen-responsive disorder in the individual being treated.

An additional method involves the use of the buccal dosage units to deliver an androgenic agent in the treatment of male sexual dysfunction, particularly erectile dysfunction, and more particularly vasculogenic erectile dysfunction. The dosage and administration period will vary depending on the individual, the severity of sexual dysfunction; however, in general, the preferred dosage and treatment regimen is as described above for hormone replacement therapy and the like. That is, for testosterone, it is generally preferred that the daily dosage be in the range of 4 mg to 10 mg, with, again, 12-hour dosage units particularly preferred.

For hormone replacement therapy, and for the other indications described herein including treatment of sexual dysfunction, the buccal dosage units are preferably used consecutively so that administration of the active agents is substantially continuous. Buccal drug administration according to the invention provides highly effective male hormone replacement therapy. That is, the disadvantages of gastrointestinal degradation and first-past inactivation of the active agents are avoided. At the same time, the side effects normally expected and encountered with conventional hormone replacement are minimized or eliminated. Preferably, for hormone replacement therapy and treatment of sexual dysfunction, the buccal dosage units are administered so that the male's natural circadian levels are simulated, with peak plasma testosterone levels occurring at about 6 a.m. to 8 a.m., decreasing thereafter for about 16–18 hours, and then increasing until the daily high is again reached.

The buccal dosage units of the present invention may be in the form of tablets made by conventional compression or molding methods. See, e.g., *Remington's Pharmaceutical Sciences*, 18th edition, (Easton, Pa.: Mack Publishing Co., 1990). Preferably, the dosage units of the present invention are prepared by mixing the components together and compressing the mixture, at a slightly elevated temperature, into tablet form. As will be appreciated by those skilled in the art, the erosion rate of the dosage unit, and thus the rate of drug delivery, is controlled by three factors: the pressure used to make the tablets, and thus the tablets' density; the carrier selected, as alluded to above; and the carrier-to-drug ratio. Pressure, carrier and carrier-to-drug ratio may thus be varied to obtain shorter acting or longer-lived dosage units. Preferred pressure for preparing the present dosage unit by compaction is in the range of approximately 500 to 2000 psi.

Figure 4:
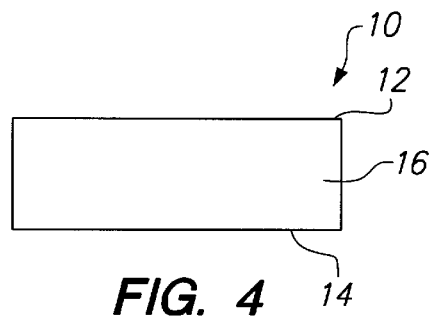
FIG. 4 schematically illustrates a preferred embodiment of a buccal dosage unit according to the invention.
Figure 6:
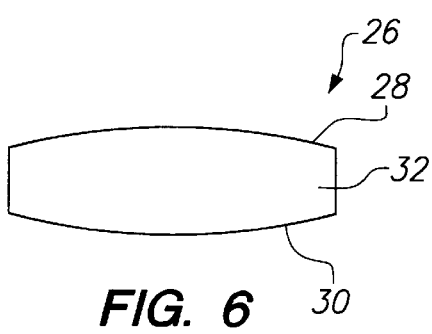
FIG. 6 schematically illustrates a second alternative embodiment of a buccal dosage unit according to the invention.
Figure 5:
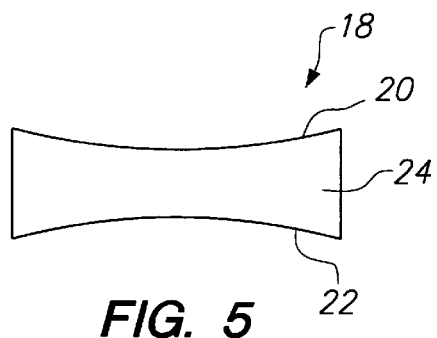
FIG. 5 schematically illustrates an alternative embodiment of a buccal dosage unit according to the invention.

The dosage units herein may have any of the conventional shapes, for example, lozenges, disks, wafers, tablets or the like. One possible configuration is a conventional tablet shape as shown in FIG. 4, with the dosage unit indicated generally at 10, the pharmaceutical composition per se shown at 12, and the dosage unit's two parallel substantially planar surfaces shown at 14 and 16; either surface can be used to affix the unit to the buccal mucosa. A more preferred configuration is shown in FIG. 5, wherein the dosage unit is shown generally at 18 with the composition at 20, and the two opposing concave surfaces at 22 and 24; the opposing concave surfaces allow for a suction effect and improve adhesion of the unit to the mucosal tissue. A less preferred configuration is shown in FIG. 6, wherein the dosage unit shown generally at 26, containing pharmaceutical composition 28, has opposing convex surfaces 30 and 32.

The dosage unit should have dimensions which fit conveniently into the buccal cavity, and, as emphasized elsewhere herein, is preferably quite compact. By way of example, suitable dimensions for the dosage unit are 2 mm to about 5 mm in diameter, preferably not exceeding about 5 mm in diameter, and about 0.3 to about 2 mm in thickness, preferably about 0.5 to 1.5 mm in thickness, most preferably about 0.5 to 1.1 mm in thickness. The total weight of the dosage unit may be from about 5 mg to about 20 mg, preferably 10 mg to about 15 mg.

Figure 7:
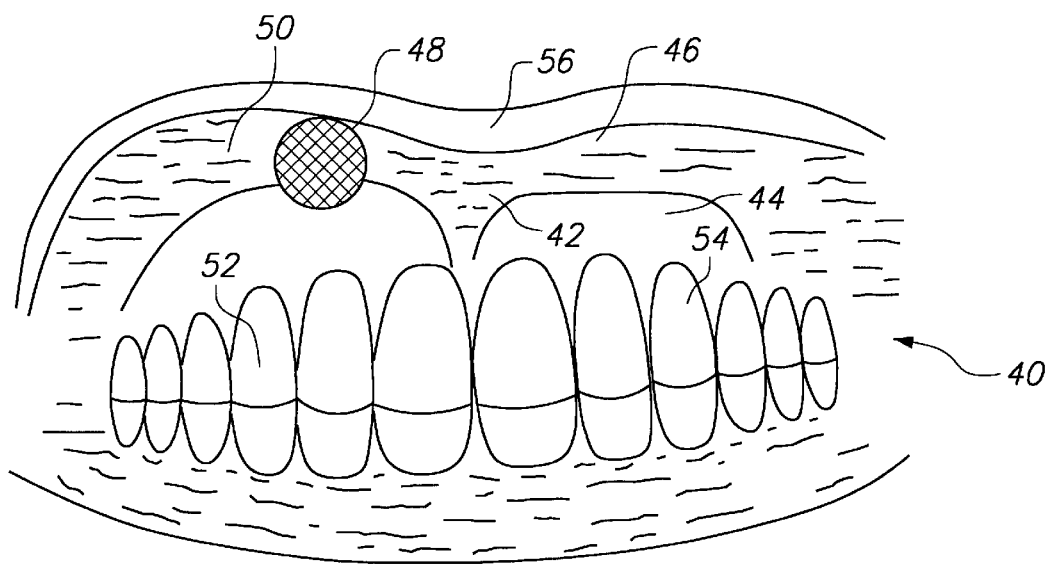
FIG. 7 illustrates placement of the buccal dosage unit in the preferred location in the oral cavity, on the upper gum area in a region defined as extending from the first bicuspid on the left to the first bicuspid on the right.

The preferred position for placement of the dosage unit in the buccal cavity, as illustrated in FIG. 7, is in the oral vestibule, generally indicated at 40, on the anterior surface 42 of the gum, between the marginal gingiva 44 and the reflexion of the mucosa from the lips to the gums 46, i.e., the dosage unit 48 is preferably attached to the alveolar mucosa 50, between the two bicuspids 52 and 54 and slightly to one side of the medial plane defined thereby. Such positioning places the dosage unit in contact with the mucosa on the internal surface of the lips 56 as well as the alveolar mucosa 50. Such placement provides advantages for optimal drug delivery. For example, when so positioned, the dosage unit is out of the salivary flow path and is less likely to detach from the gum during eating or drinking. Being out of the salivary flow path allows optimal direct transmucosal delivery of the active agents, any saliva that contacts the unit resulting not in dissolution of the active agent but, primarily, in softening the carrier. In addition, positioning the dosage unit as described minimizes mobility of the active agent in the mouth. Furthermore, the dosage unit will be in contact with both the alveolar mucosa and the internal mucosal surface of the lips, resulting in hydrolysis of the carrier, and thus absorption of the active agents through mucosa, on both sides of the tablet.

The invention also encompasses a kit for patients to carry out the aforementioned methods. The kit contains the drug to be administered in a buccal dosage unit (e.g., as shown in FIG. 4), a sealed container housing the dosage unit prior to use, and written instructions for drug administration.

The present invention thus provides a new drug delivery platform for administering pharmacologically active agents. A number of important and heretofore unrealized advantages have now been achieved:

the dosage units of the invention are highly compact, minimizing the possibility of patient discomfort;

the dosage units adhere well to the buccal mucosa and the potential for detachment during drug delivery is minimal;

the dosage units enable administration of therapeutically effective amounts of potent active agents that have low oral bioavailability;

the dosage units are efficient in that bio-erosion, i.e., hydrolysis, occurs on both sides of the buccal tablet following affixation to the buccal mucosa;

the dosage units completely hydrolyze, leaving no backing layer in the mouth;

duration of the drug delivery period is easy to control by simply adjusting the compaction pressure during manufacture and/or the size of the dosage unit; and with delivery of an androgenic agent, particularly testosterone, the dosage unit enables ready simulation of a mammalian male's circadian plasma levels, in turn facilitating treatment of male sexual dysfunction and optimizing male hormone replacement therapy.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

EXAMPLE 1

Buccal dosage units weighing approximately 10 mg to 15 mg each and containing testosterone as the active agent were prepared using a tablet direct press, as follows.

| "T1-1" Tablet Composition | |
|---|---|
| % BY WEIGHT | COMPONENT |
| 70% | Testosterone (USP, micronized, Pharmacia, Upjohn) |
| 29.8% | Polyethylene oxide (Polyox ® WSR-303, Union Carbide) |
| 0.2% | Magnesium Stearate |
| 100% | |

All components (i.e., testosterone, polyethylene oxide and magnesium stearate, as set forth in the above table) were thoroughly mixed prior to tablet formation using aqueous fluid bed granulation to provide a homogeneous mixture of active agent, polymer, and lubricant. The individual dosage units were then made by applying approximately 10 to 15 mg of the mixture into the punch die of the tablet press, and compressing the mixed components using a pressure in the range of approximately 500 to 2000 psi. Tablets having a diameter of approximately 4 mm and a height of 1 mm were prepared. The tablet was removed from the punch die and the weight and dimensions of the tablet were measured.

EXAMPLE 2

Buccal dosage units similar to those prepared in Example 1, but containing a mixture of polymeric carriers, were prepared using a tablet direct press, as follows.

| "T2-1" Tablet Composition | |
|---|---|
| % BY WEIGHT | COMPONENT |
| 70% | Testosterone (USP, micronized, Pharmacia Upjohn) |
| 20% | Polyethylene oxide (Polyox ® WSR-303, Union Carbide) |
| 9.8% | Carbomer (Carbopol ®, NF) |
| 0.2% | Magnesium Stearate |
| 100% | |

EXAMPLE 3

In Vivo Evaluation

Testosterone was administered to a male individual using a buccal dosage unit described in Example 1 (T1-1). Plasma samples were collected and analyzed for total testosterone, free testosterone, dihydrotestosterone and estradiol levels prior to treatment and at four-hour intervals after the start of treatment. The method was repeated using the same individual and the buccal dosage unit prepared as in Example 2 (T2-1). Finally, the method was repeated using the same individual and a placebo.

Figure 2:
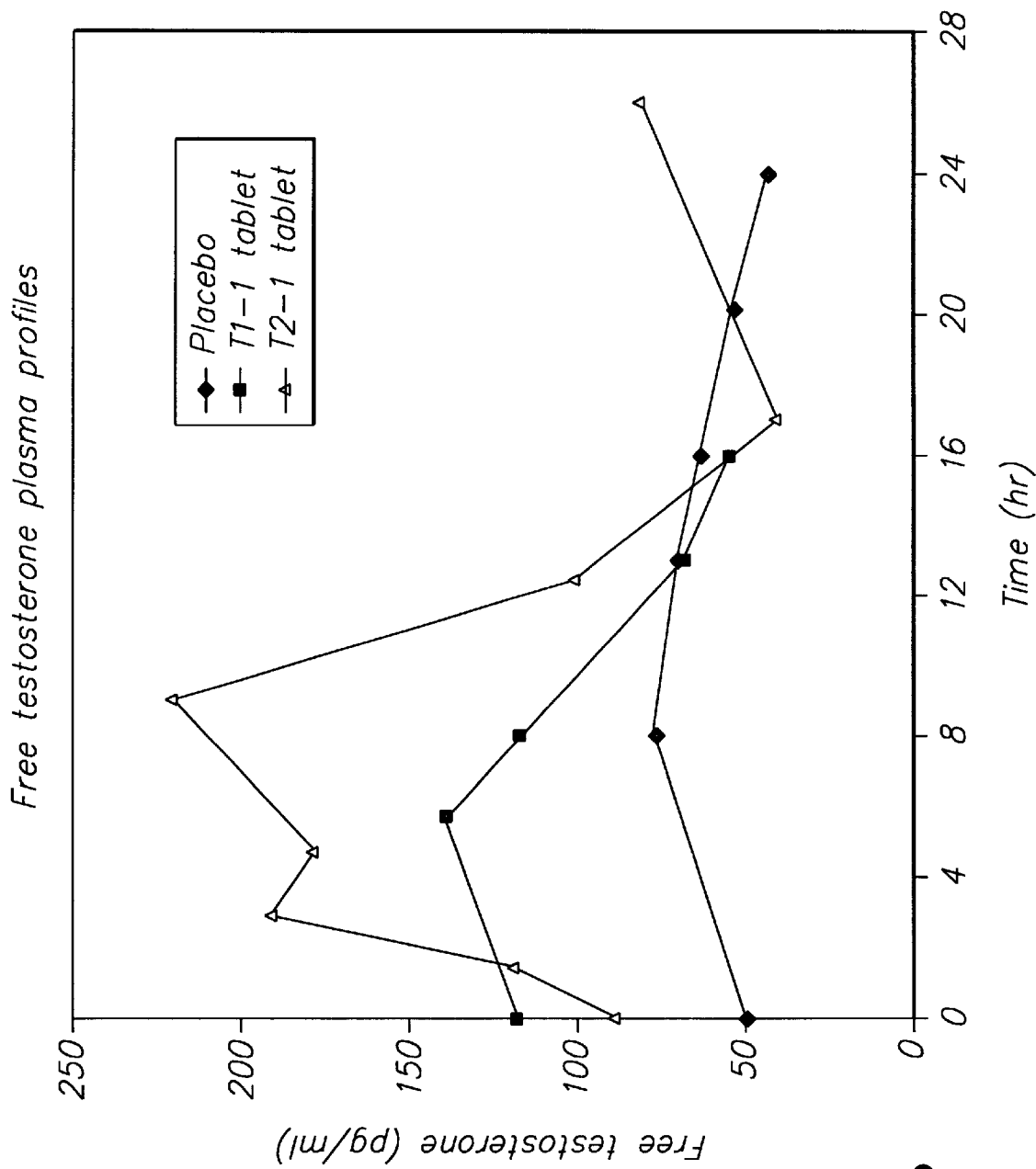
FIG. 2 is a graph illustrating free testosterone plasma levels as a function of time, following administration of either a placebo or a T1-1 or T2-1 buccal testosterone tablet, also as described in Example 3.
Figure 3:
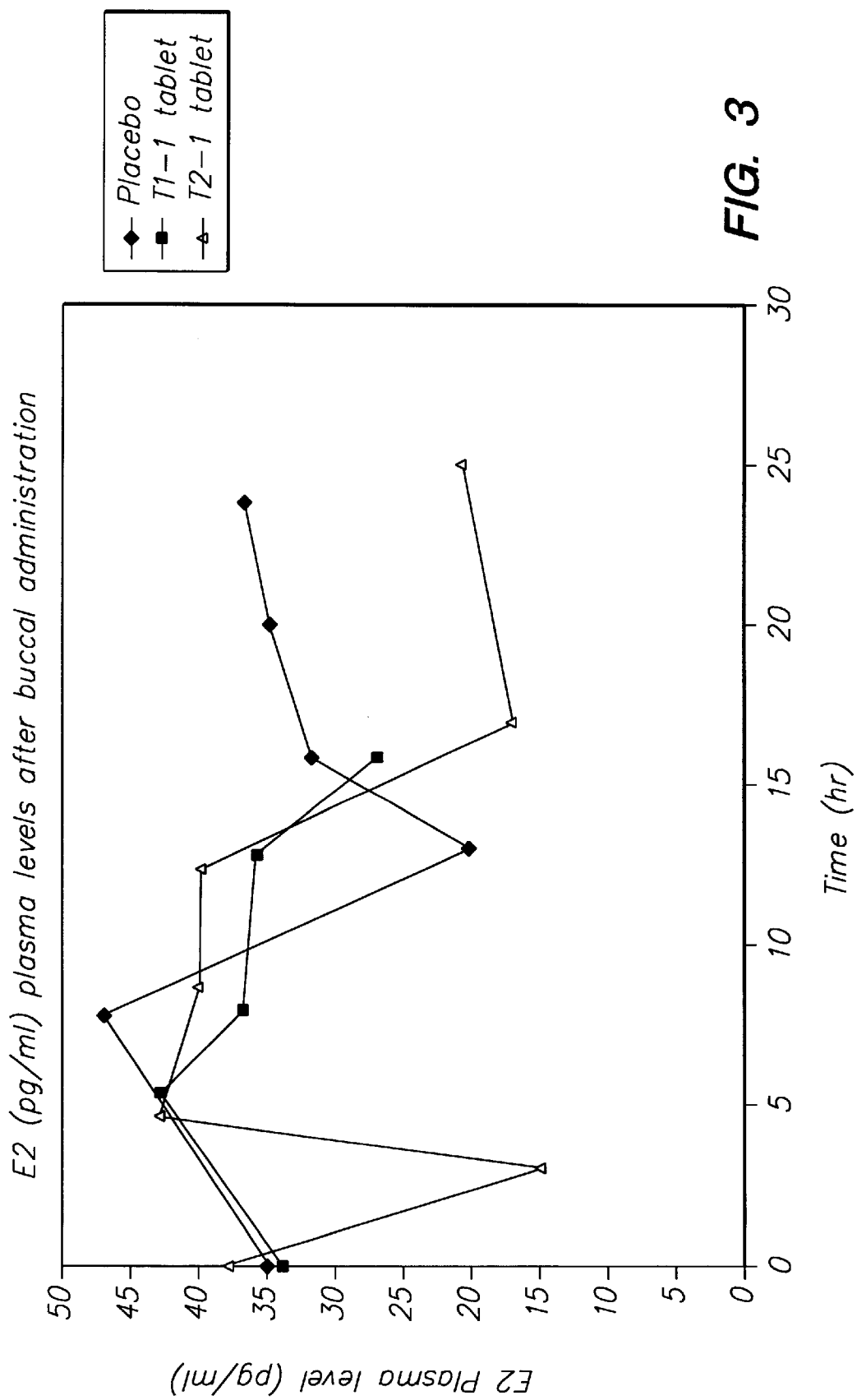
FIG. 3 is a graph illustrating estradiol plasma levels as a function of time, following administration of either a placebo or a T1-1 or T2-1 buccal testosterone tablet, also as described in Example 3.

As shown in FIGS. 1–3, the results suggest that the increase in testosterone level following buccal administration is comparable to that obtained with transdermal testosterone administration, i.e., therapeutic testosterone levels can be obtained. Normal levels of the metabolites dihydrotestosterone and estradiol were found as well, which is also desirable in hormone replacement therapy.

What is claimed is:

1. A compact buccal dosage unit for administering a pharmacologically active agent, comprising a compressed tablet of a substantially uniform mixture of a bioerodible polymeric carrier which upon sustained contact with the buccal mucosa completely erodes within a predetermined drug delivery period in the range of approximately 4 to 24 hours, and, incorporated therein, a therapeutically effective amount of a pharmacologically active agent, wherein the total weight of the unit is less than about 40 mg, the pharmacologically active agent represents at least about 40% of the total weight of the unit and the unit does not contain a disintegrant.

2. The dosage unit of claim 1, wherein the pharmacologically active agent is a macromolecular drug selected from the group consisting of proteins, peptides, and combinations thereof.

3. The dosage unit of claim 2, wherein the pharmacologically active agent is a peptide drug.

4. The dosage unit of claim 1, wherein the pharmacologically active agent is an androgenic agent.

5. The dosage unit of claim 4, wherein the androgenic agent is selected from the group consisting of androsterone, testosterone, dehydroepiandrosterone (DHEA), 4-dihydrotestosterone (DHT), methyl testosterone, testolactone, oxymetholone, fluoxymesterone, pharmaceutically acceptable esters thereof, and combinations of any of the foregoing.

6. The dosage unit of claim 5, wherein the androgenic agent is testosterone or a pharmaceutically acceptable ester thereof.

7. The dosage unit of claim 6, wherein the androgenic agent is a testosterone ester.

8. The dosage unit of claim 7, wherein the testosterone ester is selected from the group consisting of testosterone enanthate, propionate, cypionate, phenylacetate, acetate, buciclate, heptanoate, decanoate, undecanoate, caprate and isocaprate.

9. The dosage unit of claim 8, wherein the testosterone ester is selected from the group consisting of testosterone enanthate, propionate and cypionate.

10. The dosage unit of claim 6, wherein the androgenic agent is testosterone.

11. The dosage unit of claim 1, wherein the carrier is selected from the group consisting of carbomers, hydrolyzed polyvinylalcohol, polyethylene oxide, polyacrylates, hydroxypropylmethylcellulose, hydroxypropylcellulose, and combinations thereof.

12. The dosage unit of claim 11, wherein the carrier is polyethylene oxide.

13. The dosage unit of claim 11, wherein the carrier is a carbomer.

14. The dosage unit of claim 1, weighing in the range of approximately 5 mg to 20 mg.

15. The dosage unit of claim 14, weighing approximately 10 mg to 15 mg.

16. The dosage unit of claim 1, wherein the pharmacologically active agent represents approximately 40 to 80% of the total weight of the unit.

17. The dosage unit of claim 14, wherein the pharmacologically active agent represents approximately 40 to 80% of the total weight of the unit.

18. The dosage unit of claim 15, wherein the pharmacologically active agent represents approximately 40 to 80% of the total weight of the unit.

19. The dosage unit of claim 1, wherein the pharmacologically active agent represents approximately 50 to 75% of the total weight of the unit.

20. The dosage unit of claim 14, wherein the pharmacologically active agent represents approximately 50 to 75% of the total weight of the unit.

21. The dosage unit of claim 15, wherein the pharmacologically active agent represents approximately 50 to 75% of the total weight of the unit.

22. The dosage unit of claim 1, further including an effective amount of a lubricant.

23. The dosage unit of claim 22, wherein the lubricant is magnesium stearate.

24. The dosage unit of claim 1, comprising a tablet having a concave surface for contacting the buccal mucosa and adhering thereto.

25. A compact buccal dosage unit for the administration of testosterone, the dosage unit comprising a compressed tablet of a substantially uniform mixture of a bioerodible polymeric carrier which upon sustained contact with the buccal mucosa completely erodes within a predetermined drug delivery period in the range of approximately 8 to 24 hours, and, incorporated therein, a therapeutically effective amount of testosterone, wherein the total weight of the unit is in the range of about 5 mg to 20 mg, the testosterone represents approximately 40 wt. % to 80 wt. % of the total weight of the unit, and the unit does not contain a disintegrant.

26. The dosage unit of claim 25, comprising a 10 to 15 mg tablet containing approximately 50 wt. % to 75 wt. % testosterone.

27. The dosage unit of claim 25, further comprising approximately 0.01 wt. % to 2.0 wt. % of a lubricant.

28. The dosage unit of claim 26, further comprising approximately 0.01 wt. % to 2.0 wt. % of a lubricant.

29. A method for administering a pharmacologically active agent to a mammalian individual, comprising affixing the dosage unit of claim 1 to the buccal mucosa of the individual and allowing the dosage unit to remain in place until erosion thereof is complete.

30. A method for administering a pharmacologically active agent to a mammalian individual, comprising affixing the dosage unit of claim 1 to the buccal mucosa of the individual in a region of the upper gum between the first bicuspid on the left and the first bicuspid on the right.

31. A method for effecting hormone replacement therapy in a mammalian male individual, comprising buccally administering an androgenic agent to an individual in need of such treatment, wherein administration is carried out by affixing the dosage unit of claim 4 to the buccal mucosa of the individual and allowing the dosage unit to remain in place until erosion thereof is complete.

32. A method for treating sexual dysfunction in a mammalian male individual, comprising buccally administering an androgenic agent to an individual in need of such treatment, wherein administration is carried out by affixing the dosage unit of claim 4 to the buccal mucosa of the individual and allowing the dosage unit to remain in place until erosion thereof is complete.

33. A method for treating an individual suffering from an androgen-responsive disorder, comprising buccally administering an androgenic agent to the individual by affixing the dosage unit of claim 4 to the buccal mucosa and allowing the dosage unit to remain in place until erosion thereof is complete.

34. The method of claim 33, wherein the androgen-responsive disorder is hypogonadism.

35. A method for administering a macromolecular drug to a mammalian individual, comprising affixing the dosage unit of claim 2 to the buccal mucosa of the individual and allowing the dosage unit to remain in place until erosion thereof is complete.

36. A method for administering a peptide drug to a mammalian individual, comprising affixing the dosage unit of claim 3 to the buccal mucosa of the individual and allowing the dosage unit to remain in place until erosion thereof is complete.

37. The dosage unit of claim 11, wherein the carrier is comprised of a combination of polyethylene oxide and a carbomer.

38. The dosage unit of claim 37, wherein the polyethylene oxide and the carbomer are in an approximately 1:5 to 5:1 ratio by weight.

* * * * *